US012694955B2

(12) United States Patent
Yin et al.

(10) Patent No.: US 12,694,955 B2
(45) Date of Patent: Jul. 28, 2026

(54) COMPUTERIZED SYSTEM FOR INCREASING COMPUTATIONAL EFFICIENCY IN EVALUATION AND SELECTING PROPENSITY SCORE MODELS

(71) Applicant: Medidata Solutions, Inc., New York, NY (US)

(72) Inventors: Xiang Yin, New York, NY (US); Ruthanna Davi, New York, NY (US); Chengrui Huang, New York, NY (US); Benjamin Miller, New York, NY (US)

(73) Assignee: Medidata Solutions, Inc., New York, NY (US)

( * ) Notice: Subject to any disclaimer, the term of this patent is extended or adjusted under 35 U.S.C. 154(b) by 84 days.

(21) Appl. No.: 18/625,673

(22) Filed: Apr. 3, 2024

(65) Prior Publication Data

US 2025/0316346 A1 Oct. 9, 2025

(51) Int. Cl.
*G16H 10/20* (2018.01)
*G16H 50/70* (2018.01)

(52) U.S. Cl.
CPC .............. *G16H 10/20* (2018.01); *G16H 50/70* (2018.01)

(58) Field of Classification Search
CPC ................................ G16H 10/20; G16H 50/70
See application file for complete search history.

(56) References Cited

U.S. PATENT DOCUMENTS

| | | | | |
|---|---|---|---|---|
| 11,715,565 B2 * | 8/2023 | Hafez | ..................... | G06N 5/01 |
| | | | | 600/300 |
| 12,112,839 B2 * | 10/2024 | Colley | .................. | G16H 20/10 |

FOREIGN PATENT DOCUMENTS

| | | | | |
|---|---|---|---|---|
| WO | WO-2020234388 A1 * | 11/2020 | ............. | G16H 10/20 |

OTHER PUBLICATIONS

Austin, PC "An Introduction to Propensity Score Methods for Reducing the Effects of Confounding in Observational Studies." Multivariate Behavioral Research 46.3 (2011): 399. (Year: 2011).*
Rosenbaum et al., "Constructing a Control Group Using Multivariate Matched Sampling Methods That Incorporate the Propensity Score," The American Statistician, Feb. 1985, 39(1):33-38.
Stuart, "Matching Methods for Causal Inference: A Review and a Look Forward," Statistical Science: A review journal of the Institute of Mathematical Statistics, Feb. 2010, 25(1):1-21.

(Continued)

*Primary Examiner* — Eliza A Lam
(74) *Attorney, Agent, or Firm* — Fish & Richardson P.C.

(57) ABSTRACT
In an example method, a computer system accesses first data representing a plurality of characteristics of test subjects, and second data representing a plurality of candidate propensity score models that can be used for estimating an effectiveness of a treatment. The system selects a set of propensity score models by sequentially evaluating at least some of the candidate propensity score models until one or more stop criteria are satisfied. The effectiveness of the treatment can be estimated by utilizing the selected set of propensity score models. Further, the system stores a data structure representing the set of propensity score models, and outputs the data structure.

20 Claims, 5 Drawing Sheets

400

Access, from one or more hardware storage devices:
(i) first data representing a plurality of characteristics of each of a plurality of test subjects, and
(ii) second data representing a plurality of candidate propensity score models for estimating an effectiveness of a treatment of one or more of the plurality of test subjects
(402)

Select a set of propensity score models from among the plurality of candidate propensity score models (404), including
(i) sequentially evaluating at least some of the candidate propensity score models until one or more stop criteria are satisfied (404a)
(ii) selecting the set of propensity score models based on the sequential evaluation of at least some of the candidate propensity score models (404b)

Store a data structure representing the set of propensity score models using the one or more hardware storage devices
(406)

Output the data structure, including causing a user interface to be presented to a user, the user interface including an indication of the set of propensity score models
(408)

Estimate the effectiveness of the treatment based on the set of propensity score models
(410)

(56)             References Cited

OTHER PUBLICATIONS support.sas.com [online], "SAS/STAT® 15.1 User's Guide: The PSMATCH Procedure," Nov. 2018, retrieved on Oct. 4, 2024, retrieved from URL<https://support.sas.com/documentation/onlinedoc/stat/151/psmatch.pdf>, 128 pages.

Belitser et al., "Measuring balance and model selection in propensity score methods," Pharmacoepidemiology and Drug Safety, Nov. 2011, 20(11):1115-1129.

Extended European Search Report in European Appln. No. 25167087.3, mailed on Jul. 22, 2025, 12 pages.

* cited by examiner

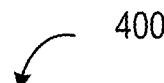

400

Access, from one or more hardware storage devices:
(i) first data representing a plurality of characteristics of each of a plurality of test subjects, and
(ii) second data representing a plurality of candidate propensity score models for estimating an effectiveness of a treatment of one or more of the plurality of test subjects
(402)

Select a set of propensity score models from among the plurality of candidate propensity score models (404), including
(i) sequentially evaluating at least some of the candidate propensity score models until one or more stop criteria are satisfied (404a)
(ii) selecting the set of propensity score models based on the sequential evaluation of at least some of the candidate propensity score models (404b)

Store a data structure representing the set of propensity score models using the one or more hardware storage devices
(406)

Output the data structure, including causing a user interface to be presented to a user, the user interface including an indication of the set of propensity score models
(408)

Estimate the effectiveness of the treatment based on the set of propensity score models
(410)

FIG. 4

COMPUTERIZED SYSTEM FOR INCREASING COMPUTATIONAL EFFICIENCY IN EVALUATION AND SELECTING PROPENSITY SCORE MODELS

TECHNICAL FIELD

This description generally relates to systems and methods for automatically evaluating and selecting propensity score models to increase the computation efficiency of a computer system.

BACKGROUND

In general, clinical trials are prospective biomedical or behavioral research studies that are designed to answer specific questions about biomedical or behavioral interventions. For example, clinical trials can be performed to evaluate the safety and/or efficacy of vaccines, drugs, dietary choices, dietary supplements, and/or medical devices.

SUMMARY

A computer system can be configured to automatically evaluate and select propensity score models, such as those used in analyzing the results of clinical trials.

In general, propensity score models are used to generate propensity scores that can be used in matching or weighting, a statistical technique that attempts to estimate the effect of a treatment, policy, or other intervention by accounting for the covariates that are considered as confounding. For example, propensity score methods can be used to reduce confounding bias, that is selection of experimental and control subjects completed in such a way that the subject characteristics are systematically different across treatment groups, perhaps with those with better prognosis preferentially receiving one therapy over another.

In an example implementation, a computer system may create a list of a large number of propensity score models with which to analyze the results of a clinical trial. Each of the propensity score models may differ in their suitability and effectiveness in estimating the association between treatment status (e.g., "exposure") and the observed characteristics of a subject (e.g., "covariates"). The computer system can evaluate at least some of the propensity score models and select one or more propensity score models that are particularly suitable or effective in evaluating a particular set of results. Further, information regarding the selected propensity score models can be stored for future retrieval and/or presented to a user (e.g., to facilitate the analysis of a clinical trial).

In some implementations, the computer system can be configured to automatically evaluate and select propensity score models by prioritizing the evaluation of some propensity score models over others and discontinue evaluation when one or more suitable propensity score models are identified. For example, the computer system can be configured to sequentially evaluate propensity score models (e.g., in order of complexity, such as from least complex to most complex) until one or more stop criteria are met (e.g., indicating that one or more suitable propensity score models have been identified). Further, the computer system can output one or more data structures representing the identified propensity score models.

The implementations described herein can provide various technical benefits. As an example, the implementations described herein allow a computer system to automatically evaluate and select propensity score models in a particularly efficient manner. For example, in a typical technique, a computer system may evaluate each and every available propensity score model and select one or more propensity score models based on the evaluation. However, this technique may consume a large amount of computer resources (e.g., processing utilization, memory utilization, data storage utilization, etc.), due to the brute force nature of the evaluation. In contrast, as described herein, a computer system can instead sequentially evaluate propensity score models and discontinue evaluating propensity score models when one or more stop criteria are met (e.g., indicating that one or more suitable propensity score models have been identified). Thus, in at least some implementations, the computer system need not evaluate each and every available propensity score model, and thus can reduce the computer resources that are consumed (e.g., compared to those that would be consumed according to a traditional technique).

As another example, the implementations described herein can be used to improve the analysis of clinical trial results (e.g., by selecting and utilizing a propensity score model that is particularly suitable for analyzing the results). This allows researchers to better assess the effectiveness of medical interventions, thereby improving the safety and/or efficacy of the treatment of subjects. For example, the techniques described herein can be used to better understand the effectiveness of a treatment, and to modify the treatment to further improve its efficacy. Further, this reduces the likelihood that clinical trial results would be misinterpreted or otherwise analyzed improperly, thereby improving the efficiency by which treatments are researched and developed (e.g., by reducing the amount of resources that would be consumed in pursuing research and development goals that are based on a misinterpretation of the clinical trial studies and/or an improper analysis of the clinical trial results).

As another example, the implementations described herein can be used to provide a structured data file for storing information regarding the evaluation of propensity score models and presenting such information to a user in an organized and easily understood manner. Accordingly, users can intuitively determine the suitability of each of the evaluated propensity score models, and select one or more of the propensity score models to facilitate the analysis of a clinical study.

In an aspect, a system includes: user interface circuitry for generating a user interface that, when rendered on a display device, includes one or more visual representations of a tabular structured data file including a grid of data cells; a memory for storing: first data representing a plurality of characteristics of each of a plurality of test subjects, and second data representing a plurality of candidate propensity score models for estimating an effectiveness of a treatment performed on one or more of the test subjects; a processor communicatively coupled to the at least one memory, where the processor is configured to: access, from the memory, the first data and the second data; select a set of propensity score models from among the plurality of candidate propensity score models, where selecting the set of propensity score models includes: sequentially evaluating at least some of the candidate propensity score models until one or more stop criteria are satisfied, where evaluating each of the candidate propensity score models includes: obtaining an output of the candidate propensity score model based in at least a portion of the first data as input, and determining whether the output of the candidate propensity score model satisfies the one or more stop criteria; and selecting the set of propensity score models based on the sequential evaluation of at least some of the candidate propensity score models; and store, using the memory, the tabular structured data file representing the set of propensity score models; output the tabular structured data file, where outputting the tabular structured data file includes causing the user interface to be presented to a user using the user interface circuitry and the display device, where the user interface includes an indication of the set of propensity score models.

In an aspect, a method includes: accessing, by a computer system from one or more hardware storage devices: first data representing a plurality of characteristics of each of a plurality of test subjects, and second data representing a plurality of candidate propensity score models that can be used for estimating an effectiveness of a treatment of one or more of the plurality of test subjects; and selecting a set of propensity score models from among the plurality of candidate propensity score models. Selecting the set of propensity score models includes: sequentially evaluating at least some of the candidate propensity score models until one or more stop criteria are satisfied, where evaluating each of the candidate propensity score models includes: obtaining an output of the candidate propensity score model based in at least a portion of the first data as input, and determining whether the output of the candidate propensity score model satisfies the one or more stop criteria. Selecting the set of propensity score models also includes selecting the set of propensity score models based on the sequential evaluation of at least some of the candidate propensity score models. The method also includes storing, by the computer system, a data structure representing the set of propensity score models using the one or more hardware storage devices; outputting, by the computer system, the data structure, where outputting the data structure includes causing, by the computer system, a user interface to be presented to a user, where the user interface includes an indication of the set of propensity score models.

Implementations of this aspect can include one or more of the following features.

In some implementations, the method can also include estimating the effectiveness of the treatment based on the set of propensity score models.

In some implementations, the method can also include conducting a clinical study based on the data structure.

In some implementations, the method can also include modifying the treatment of one or more additional subjects based on the data structure.

In some implementations, the set of propensity score models can include a single propensity score model only.

In some implementations, the set of propensity score models can include a plurality of propensity score models.

In some implementations, sequentially evaluating at least some of the candidate propensity score models can include determining a sequential order for the candidate propensity score models, and evaluating at least some of the candidate propensity score models based on the sequential order.

In some implementations, the sequential order can be determined based on a complexity of each of the candidate propensity score models.

In some implementations, the sequential order can be determined based on a statistical complexity of each of the candidate propensity score models.

In some implementations, the output of the candidate propensity score model can represent a standardized difference of each of one or more covariates of the candidate propensity score model.

In some implementations, the one or more stop criteria can include a determination that the standardized difference of each of the one or more covariates of the candidate propensity score model is less than a threshold value.

In some implementations, the one or more stop criteria can include a determination that a number of evaluated candidate propensity score models is greater than or equal to a threshold value.

In some implementations, the data structure can include a tabular structured data file including a grid of data cells, where the data cells are arranged according to a plurality of rows and a plurality of columns, and where the data cells represent: at least one of the candidate propensity score models, and at least one of the standardized differences corresponding to the at least one of the candidate propensity score models.

In some implementations, the method can include receiving user input representing one or more selection criteria, and selecting at least some of the candidate propensity score models based on the one or more selection criteria.

In some implementations, each of the candidate propensity score models can be configured to generate a respective propensity score based on at least a portion of the first data, and where the propensity score represents a probability that a particular test subject has been administered the treatment based on the characteristics of that test subject.

In some implementations, estimating the effectiveness of the treatment of the clinical study can include minimizing, based on the at least one propensity score model of the set of propensity score models, a selection bias associated with an estimation of an effect of the treatment.

Other embodiments of this aspect include corresponding computer systems, apparatuses, and computer programs recorded on one or more computer storage devices, each configured to perform the actions of each of the chat agent, the triage agent, and the retrieval agent. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by a data processing apparatus, causes the apparatus to perform the actions.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 4 is a flow chart diagram of an example process for automatically evaluating and selecting propensity score models.

Like reference numbers and designations in the various drawings indicate like elements.

DETAILED DESCRIPTION

Figure 1:
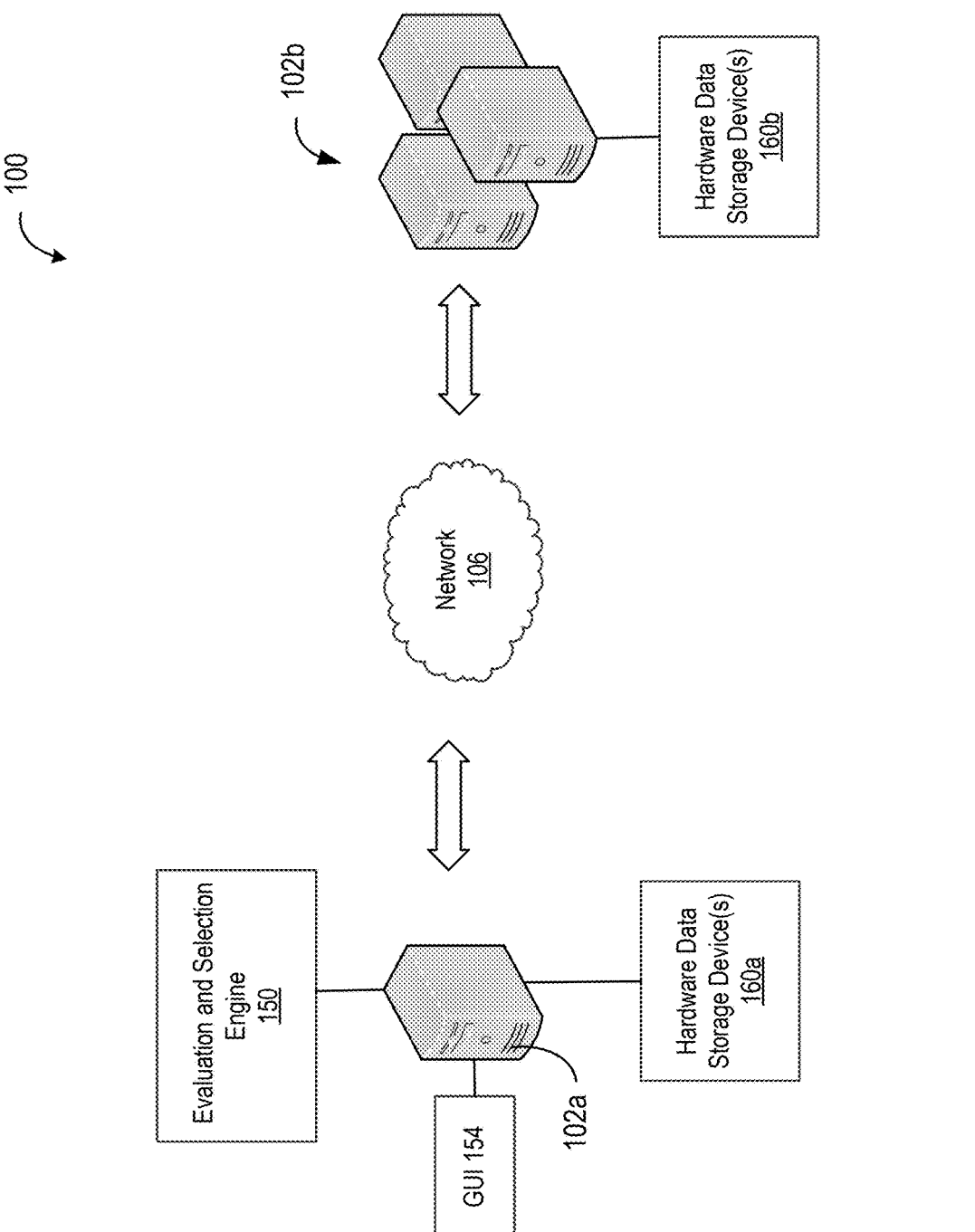
FIG. 1 is a diagram of an example system for automatically evaluating and selecting propensity score models.

FIG. 1 shows an example system 100 for automatically evaluating and selecting propensity score models, such as those used in analyzing the results of clinical trials. For example, the system 100 can receive clinical trial data (e.g., baseline characteristics), and automatically evaluate and select one or more propensity score models based on the clinical trial data (e.g., one or more propensity score models that are particularly suitable for balancing baseline characteristics). Further, the system 100 can output data structures representing the selected propensity score models.

The system 100 includes an evaluation and selection engine 150 implemented on a computer system 102*a*. In general, the engine 150 is configured to obtain data representing propensity score models available to the system 100 and evaluate at least some of the propensity score models (e.g., to determine the suitability of each of the evaluated propensity score models in analyzing a particular set of clinical trial data). Further, in at least some implementations, the engine 150 can select one or more of the evaluation propensity score models (e.g., propensity score models that are particularly suitable for analyzing the set of clinical trial data) and present the selected propensity score models to a user.

For instance, during an example operation of the system 100, the engine 150 obtains a set of clinical trial data. As an example, the set of clinical trial data can represent the characteristics of each of the subjects of the clinical trial (e.g., the subjects' age, medical condition, medical history, demographic information, etc.). As another example, the set of clinical trial data can represent the treatment statuses of each of the subjects (e.g., whether each of the subjects was selected for a treatment—and if so the type of treatment, whether each of the subjects was selected for a placebo treatment, etc.). In some implementations, the set of clinical trial data can be implemented, at least in part, as one or more portions of structured data.

Further, the engine 150 can obtain model data representing propensity score models that are available for analyzing the set of clinical trial data. In general, propensity score models are used to generate propensity scores that can be used in matching or weighting, a statistical technique that attempts to estimate the effect of a treatment, policy, or other intervention by accounting for the covariates that are considered as confounding. For example, propensity score methods can be used to reduce confounding bias, that is selection of experimental and control subjects completed in such a way that the subject characteristics are systematically different across treatment groups, perhaps with those with better prognosis preferentially receiving one therapy over another.

In at least some implementations, the possibility of bias in a clinical trial arises because of a difference in the treatment outcome (e.g., as the average treatment effect) between treated and untreated groups that may be caused by a factor that predicts treatment rather than the treatment itself. For instance, in randomized trials, the randomization allows for unbiased estimation of treatment effects. For each covariate, randomization implies that treatment groups will be balanced on average, by the law of randomization. Unfortunately, for observational studies, the assignment of treatments to research subjects is often not random. Propensity score matching and weighting attempts to reduce the treatment assignment bias and mimic randomization, by creating a sample of units that received the treatment that is comparable on all observed covariates to a sample of units that did not receive the treatment.

In particular, the "propensity score" generated by a propensity score model represents how likely a subject is to have been treated, given their covariate values. The stronger the confounding effects of covariates—that is, the stronger the covariates are associated with whether a subject is treated or not and the outcome—the larger the bias in the analysis of the naive treatment effect when the covariates are imbalanced between treatment groups. By having units with similar propensity scores in both treatment and control, such confounding is reduced.

In some implementations, the model data can include one or more mathematical functions, equations, computer macros, and/or portions of computer code to generate one or more propensity scores, using a set of clinical trial data as an input. In some implementations, the model data can be implemented, at least in part, as one or more portions of structured data.

In some implementations, at least some of the clinical trial data and/or model data can be retrieved from one or more hardware data storage devices 160*a* local to the computer system 102*a*. In some implementations, at least some of the clinical trial data and/or model data can be retrieved from one or more hardware data storage devices 160*b* remote from the computer system 102*a* (e.g., one or more remote computer systems 102*b*, such as server computers, that are communicatively coupled to the computer system 102*a* via a network 106). In some implementations, at least some of the clinical trial data and/or model data can be manually input by a user (e.g., using a graphical user interface (GUI) 154 represented by the computer system 102*a*.

Each of the propensity score models may differ in their suitability and effectiveness in estimating the association between treatment status (e.g., "exposure") and the observed characteristics of a subject (e.g., "covariates"). The engine 150 can evaluate at least some of the propensity score models (e.g., based on the clinical trial data and the model data), and select one or more propensity score models that are particularly suitable or effective in evaluating a particular set of results.

Further, data regarding the evaluation of the propensity score models and/or an indication of the selected propensity models can be stored for future retrieval and/or presented to a user (e.g., to facilitate the analysis of a clinical trial). For example, in some implementations, at least some of the data regarding the evaluation of the propensity score models and/or an indication of the selected propensity models can be stored locally on the hardware data storage devices 160*a* and/or remotely on the hardware data storage device 160*b*. As another example, in some implementations, at least some of the data regarding the evaluation of the propensity score models and/or an indication of the selected propensity models can be represented to a user via the GUI 154.

In some implementations, the engine 150 can be configured to automatically evaluate and select propensity score models by prioritizing the evaluation of some propensity score models over others and discontinue evaluation when one or more suitable propensity score models are identified.

For example, the engine 150 can determine, based on the model data, a sequence in which to evaluate the propensity score models. In some implementations, the sequence can be arranged in order of complexity (e.g., from the least complex propensity score model, to the most complex propensity score model). In some implementations, the complexity of a propensity score model can be determined based on the types of operations (e.g., statistical operations) that are performed using that propensity score model, the type of statistical relationships that are modeled (e.g., statistical relationships between covariates), and/or the amount of computer resources that would be consumed by utilizing the propensity score model.

Further, the engine 150 can be configured to evaluate propensity score models according to the determined sequence until one or more stop criteria are met (e.g., indicating that one or more suitable propensity score models have been identified).

For example, the engine 150 can be configured to evaluate propensity score models until the standardized difference of some or all of the evaluate covariates of a propensity score model are less than a threshold value (e.g., indicating that the balancing of baseline characteristics between different treatment groups is achieved to a sufficient degree after propensity score matching or weighting). This can be beneficial, for example, in allowing the engine 150 to identify one or more suitable propensity score models, without requiring that the engine 150 evaluate each and every available propensity score model (e.g., thereby reducing the computer resources that are consumed).

As another example, the engine 150 can be configured to evaluate propensity score models until a particular maximum number of propensity score models have been evaluated. Upon completion of the evaluation process, the engine 150 can select one or more of the best propensity score models that have been tested. This can be beneficial, for example, in allowing the engine 150 to limit the amount of computer resources that are consumed.

In general, the output of the engine 150 can be used to analyze the data of a clinical trial. For example, based on the output of the engine 150, a researcher can use a particular propensity score model to account for covariates that predict the receiving of treatment that was evaluated in the target clinical trial, such that they can better estimate the safety and/or efficacy of the treatment (e.g., to reduce confounding factors in subsequent analysis). Further, this allows researchers to improve the understanding of safety and/or efficacy of the treatment of interest. For example, the techniques described herein can be used to better understand the effectiveness of a treatment, and to modify the treatment to further improve its efficacy.

In general, each of the computer systems 102a and 102b can include any number of electronic devices that are configured to receive, process, and transmit data. Examples of the computer systems include client computing devices (e.g., desktop computers or notebook computers), server computing devices (e.g., server computers or cloud computing systems), mobile computing devices (e.g., cellular phones, smartphones, tablets, personal data assistants, notebook computers with networking capability), wearable computing devices (e.g., smart watches), and other computing devices capable of receiving, processing, and transmitting data. In some implementations, the computer systems can include computing devices that operate using one or more operating systems (e.g., Microsoft Windows, Apple macOS, Linux, Unix, Google Android, and Apple iOS, among others) and one or more architectures (e.g., x86, PowerPC, and ARM, among others). In some implementations, one or more of the computer systems need not be located locally with respect to the rest of the system 100, and one or more of the computer systems can be located in one or more remote physical locations.

Each of the computer systems 102a and 102b can include a respective user interface (e.g., GUI 154) that enables users to interact with the computer system, other computer systems, and/or the engine 150. Example interactions include viewing data, transmitting data from one computer system to another, and/or issuing commands to a computer system. Commands can include, for example, any user instruction to one or more of the computer systems to perform particular operations or tasks. In some implementations, a user can install a software application onto one or more of the computer systems to facilitate performance of these tasks.

In FIG. 1, the computer system 102a is illustrated as a single component. However, in practice, the computer system 102a can be implemented on one or more computing devices (e.g., each computing device including at least one processor such as a microprocessor or microcontroller). As an example, the computer system 102a can be a single computing device that is connected to the network 106, and the engine 150 can be maintained and operated on the single computing device. As another example, the computer system 102a can include multiple computing devices that are connected to the network 106, and the engine 150 can be maintained and operated on some or all of the computing devices. For instance, the computer system 102a can include several computing devices, and the engine 150 can be distributed on one or more of these computing devices.

The network 106 can be any communications network through which data can be transferred and shared. For example, the network 106 can be a local area network (LAN) or a wide-area network (WAN), such as the Internet. The network 106 can be implemented using various networking interfaces, for instance wireless networking interfaces (such as Wi-Fi, Bluetooth, or infrared) or wired networking interfaces (such as Ethernet or serial connection). The network 106 also can include combinations of more than one network and can be implemented using one or more networking interfaces.

Figure 2:
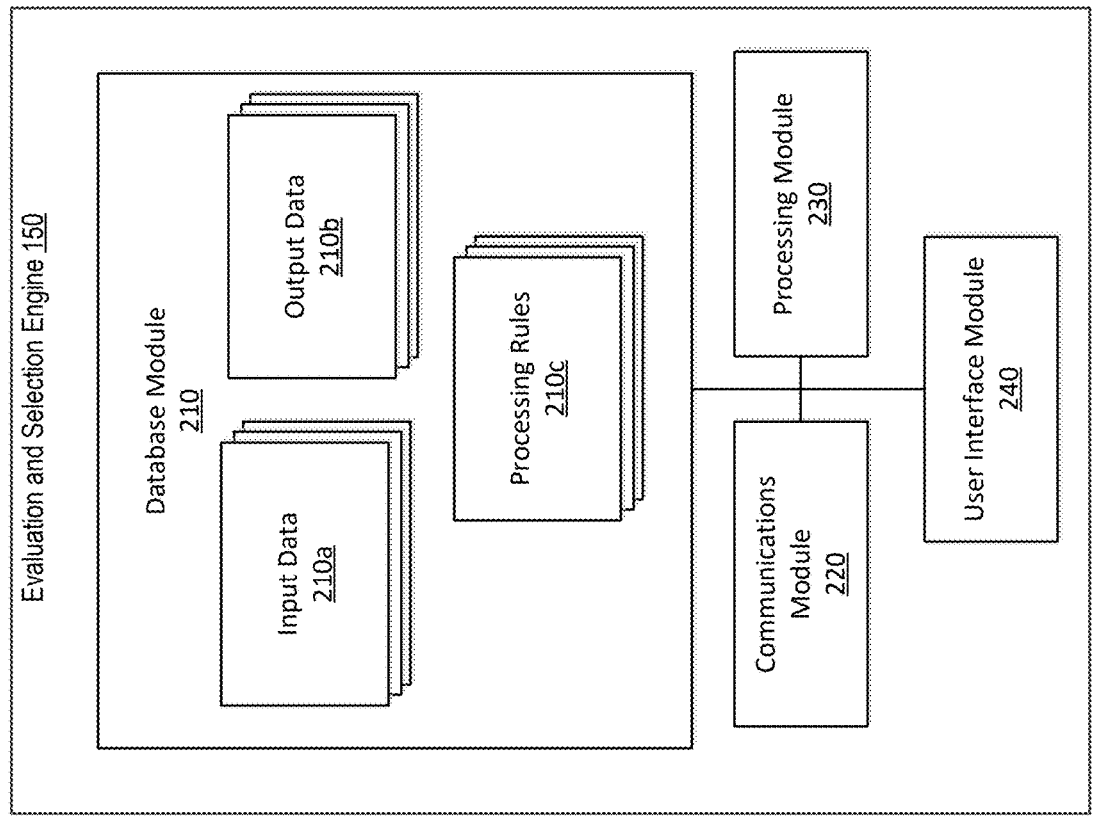
FIG. 2 is a diagram of an example evaluation and selection engine.

FIG. 2 shows various aspects of the evaluation and selection engine 150 in greater detail. In general, the engine 150 includes several operation modules that perform particular functions related to the operation of the engine 150. For example, the engine 150 includes a database module 210, a communications module 220, a processing module 230, and a user interface module 240. The operation modules can be provided as one or more computer executable software modules, hardware modules, or a combination thereof. For example, one or more of the operation modules can be implemented as blocks of software code with instructions that cause one or more processors of the engine 150 to execute operations described herein. In addition, or alternatively, one or more of the operations modules can be implemented in electronic circuitry such as, e.g., programmable logic circuits, field programmable logic arrays (FPGA), or application specific integrated circuits (ASIC).

The database module 210 maintains information related to evaluating and selecting propensity score models.

As an example, the database module 210 can store input data 210a that is used as inputs for evaluating and evaluating and selecting propensity score models.

As an example, the input data 210a can include clinical trial data (e.g., as described with reference to FIG. 1), such as data representing the characteristics of each of the subjects of a clinical trial and the treatment statuses of each of the subjects.

As another example, the input data 210a can include model data representing propensity score models that are available for analyzing the set of clinical trial data (e.g., as described with respect to FIG. 1), such as data representing one or more mathematical functions, equations, and/or portions of computer code to generate one or more propensity score models.

As another example, the input data 210a can include instructions from a user regarding the evaluation and selection of propensity score models. For instance, the input data 210a can include instructions from a user to evaluate a particular subset of propensity score models that are available to the engine 150. Further, the input data 210a can include instructions from a user to evaluate propensity score models in a particular sequential order. Further, the input data 210a can include instructions from a user to discontinue evaluating propensity score models when certain stop criteria are satisfied.

In some implementations, at least some of the input data 210a can be retrieved from one or more local hardware data storage devices (e.g., hardware data storage devices 160a) and/or remote hardware data storage devices (e.g., hardware data storage devices 160b). In some implementations, at least some of the input data 210a can be received from a user (e.g., using the GUI 154 generated by the user interface module 240).

Further, the database module 210 can store output data 210b generated by the engine 150. As an example, the output data 210b can include, for each of the evaluated propensity score model, data representing the results of the evaluation (e.g., one or more metrics that indicate the effectiveness of the propensity score model in balancing the characteristics between the group of subjects receiving the treatment of interest and the group that did not receive the treatment). For instance, the output data 210b can represent one or more covariates of the clinical trial data, and a metric (e.g., standardized difference) associated with each of the covariates.

As another example, the output data 210b can include data representing a selection of one or more propensity score models. For instance, the output data 210b can include data indicating that one or more propensity score models have met one or more criteria (e.g., indicating that one or more suitable propensity score models have been identified).

As another example, the output data 210b can filter or sort the data based on the results of the evaluations. For instance, the output data 210b can indicate each of the propensity score models that have been evaluated, and can be sorted (e.g., based on the number of subjects retained after matching, from highest to lowest). As another example, the output data 210b can indicate a subset of the propensity score models that have been evaluated (e.g., the N-best propensity score model, where N is one or more), and omit the remaining propensity score models.

Further, the database module 210 can store processing rules 210c specifying how data in the database module 210 can be processed to evaluate and select propensity score models.

As an example, the processing rules 210c can include one or more rules for identifying the propensity score models for evaluation by the engine 150, and the order in which they are to be evaluated.

As another example, the processing rules 210c can indicate how to input data into each of the available propensity score models, and how to generate output data 210b (e.g., representing the evaluation of the propensity score models) based on the inputted data.

As another example, the processing rules 210c can indicate one or more rules for determining whether to discontinue evaluation of the propensity score models (e.g., one or more rules specifying that the evaluation of propensity score models be discontinued when certain stop criteria are satisfied).

As another example, processing rules 210c can specify that the generated output data 210b be presented to the user and/or stored for future retrieval and/or processing (e.g., using the database module 210).

Example data processing techniques are described in further detail below.

As described above, the engine 150 also includes a communications module 220. The communications module 220 allows for the transmission of data to and from the engine 150. For example, the communications module 220 can be communicatively connected to the network 106, such that it can transmit data to and receive data from the computer system 102b. Information received from the computer system 102b can be processed (e.g., using the processing module 230) and stored (e.g., using the database module 210).

As described above, the engine 150 also includes a processing module 230. The processing module 230 processes data stored or otherwise accessible to the engine 150. For instance, the processing module 230 can be used to execute one or more of the operations described herein (e.g., operations associated with the evaluation and selection of propensity score models).

The user interface module 240 is configured to present information to a user and/or to receive inputs from a user. As an example, the user interface module 240 can include one or more display devices (e.g., display screens, touch screens, etc.) that are configured to present a user interface (e.g., the GUI 154) that enables users to interact with the computer system 102a and/or the engine 150. Example interactions include viewing data, transmitting data from one component to another, and/or issuing commands to the computer system 102a and/or the engine 150. Commands can include, for example, any user instruction to one or more of the computer systems 102a and/or the engine 150 to perform particular operations or tasks.

In some implementations, a software application can be used to facilitate performance of the tasks described herein. As an example, an application can be installed on the computer systems 102a. Further, a user can interact with the application to input data and/or commands to the engine 150, and review data generated by the engine 150.

Figure 3:
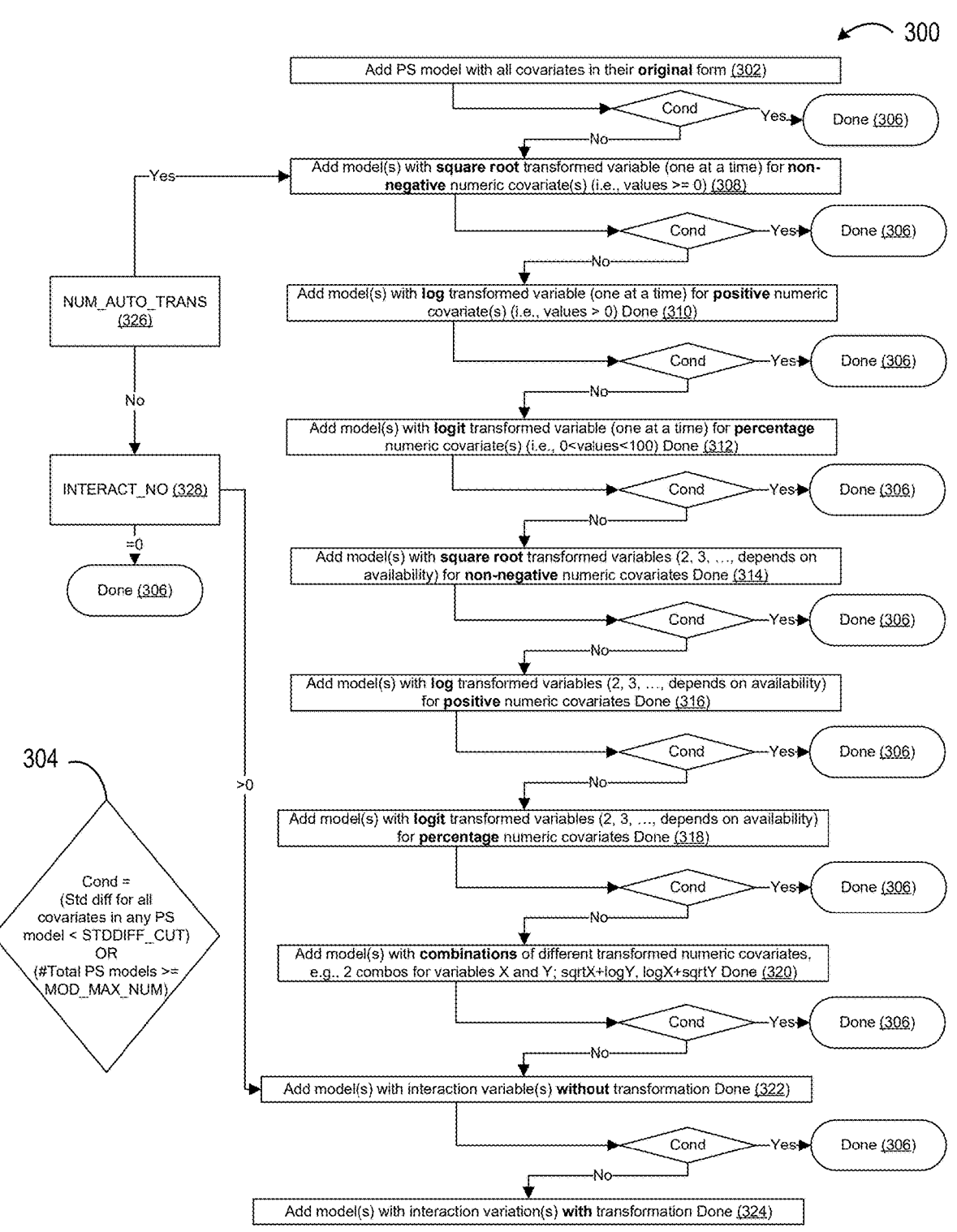
FIG. 3 is a flow chart diagram of an example process for automatically evaluating and selecting propensity score models.

As described above, a computer system (e.g., using the engine 150) can be configured to evaluate and select propensity score models by prioritizing the evaluation of some propensity score models over others, and discontinue evaluation when one or more suitable propensity score models are identified. As an example, process 300 for evaluating propensity score models is shown in FIG. 3.

In the process 300, a computer system accesses data regarding the propensity score models that are available for evaluation (e.g., candidate propensity score models), and evaluates any of the propensity score models in which a set of covariates of the clinical trial data are represented in the propensity scores model in their original form (302).

Upon performing the evaluation, the computer system determines whether one or more stop criteria have been satisfied (304). In general, the stop criteria can specify conditions that, when met, indicate that one or more suitable propensity score models have been identified.

In some implementations, the one or more stop criteria can include a criterion that is satisfied when the standardized differences of all of the evaluated covariates in an evaluated propensity score model are smaller than a threshold value (e.g., "STDDIFF_CUT").

In some implementations, the one or more stop criteria can include a criterion that is satisfied when the total number of propensity score models that have been evaluated is greater than or equal to a threshold number (e.g., "MOD_MAX_NUM").

In some implementations, the one or more stop criteria can include a combination of multiple criteria, and the stop criteria can be considered satisfied when at least one of the criteria is satisfied. For example, as shown in FIG. 3, the stop criteria can be considered satisfied when (i) the standardized differences of all of the evaluated covariates in an evaluated propensity score model are smaller than a threshold value (e.g., "STDDIFF_CUT") or (ii) the total number of propensity score models that have been evaluated is greater than or equal to a threshold number (e.g., "MOD_MAX_NUM").

If the one or more stop criteria are satisfied, the process 300 is terminated (306).

Upon termination of the process 300, the computer system generates one or more data structures representing the evaluated propensity score models. For example, the computer system can generate a report summarizing the covariates of each of the evaluated propensity score models. As another example, the computer system can select one or more propensity score models having the best performance (e.g., having the lowest standardized differences for its covariates) and indicate those propensity score models in the report.

In some implementations, the data structures can include one or more spreadsheets. For example, a data structure can include a tabular structured data file including a grid of data cells, where the data cells are arranged according to rows and columns. Further, the data cells can include information such as (i) one or more of the evaluated propensity score models, and (ii) information regarding each of those propensity score models (e.g., standardized differences for the covariates of those propensity score models, etc.). In some implementations, the data cells can be sorted and/or filtered to facilitate analysis of the propensity score models (e.g., as described above).

Upon termination of the process 300, the computer system can also generate the number and percentage of subjects matched in each treatment group using the selected propensity score models if propensity score matching is selected, or weighted number of subjects in each treatment group if propensity score weighting is selected.

If the one or more stop criteria are not satisfied, the computer system continues evaluating additional propensity score models until the one or more stop criteria are satisfied. For example, as shown in FIG. 3, the computer system can sequentially evaluate:

(i) Any propensity score models with square root transformed variable(s) (one at a time) for non-negative numeric covariate(s) (that is, covariate(s) with values>=0) (308), (ii) Any propensity score models with logarithm transformed variable(s) (one at a time) for positive numeric covariate(s) (that is, covariate(s) with values>0) (310), (iii) Any propensity score models with logit transformed variable(s) (one at a time) for percentage numeric covariate(s) (that is, covariate(s) with values between 0 and 100) (312), (iv) Any propensity score models with square root transformed variable(s) (multiple times) for non-negative numeric covariate(s) (314), (v) Any propensity score models with logarithm transformed variable(s) (multiple times) for positive numeric covariate(s) (316), (vi) Any propensity score models with logit transformed variable(s) (multiple times) for percentage numeric covariate(s) (318), and (vii) Any propensity score models with combinations of different transformed numerical covariates (e.g., two combinations for variables X and Y, such as: sqrt(X)+log(Y), log(X)+sqrt(Y), etc.) (320).

(viii) Any propensity score models with interaction variable(s) without transformation (322), and (ix) Any propensity score models with interaction variable(s) with transformation (324).

At each evaluation stage 308, 310, 312, 314, 316, 318, 320, and 322, the computer system determines whether the one or more stop criteria have been satisfied (304). If so, the process 300 is terminated (306). If not, the process 300 proceeds to the next evaluation stage in the sequence.

Upon the completion of the evaluation stage 324, the process 300 terminates, even if the one or more stop criteria have not been satisfied.

In some implementations, a user can specify that the computer system automatically generates and evaluates all of the available propensity score models with transformation (e.g., "NUM_AUTO_TRANS") (326). If this option is turned off by the user, the computer system can skip evaluating propensity score models with transformation (evaluation stages 308, 310, 312, 314, 316, 318, and 320) proceed directly from evaluation stage 302 to evaluation stage 322.

In some implementations, a user can specify that a computer system evaluates a particular subset of the available propensity score models (e.g., "INTERACT_NO") (328). If this option is specified as any non-negative integer by the user, the computer system can evaluate propensity score models with two-way interaction (evaluation stages 322 and 324) with at most the specified number of two-way interactions in each propensity score model. For example if this value is set as 1, then each model can have at most one interaction term.

Example Processes

FIG. 4 shows an example process 400 for automatically evaluating and selecting propensity score models, such as those used in analyzing the results of clinical trials. In some implementations, the process 400 can be performed by the system 100 described in this disclosure (e.g., using the engine 150).

In the process 400, a system accesses, from one or more hardware storage devices (i) first data representing a plurality of characteristics of each of a plurality of test subjects, and (ii) second data representing a plurality of candidate propensity score models that can be used for estimating an effectiveness of a treatment of one or more of the plurality of test subjects (402).

Further, the system selects a set of propensity score models from among the plurality of candidate propensity score models (404). In some implementations, each of the candidate propensity score models can be configured to generate a respective propensity score based on at least a portion of the first data. Further, the propensity score can represent a probability that a particular test subject has been administered the treatment based on the characteristics of that test subject.

Selecting the set of propensity score models includes sequentially evaluating at least some of the candidate propensity score models until one or more stop criteria are satisfied (404a). Evaluating each of the candidate propensity score models includes (i) obtaining an output of the candidate propensity score model based in at least a portion of the first data as input, and (ii) determining whether the output of the candidate propensity score model satisfies the one or more stop criteria.

In some implementations, sequentially evaluating at least some of the candidate propensity score models can include (i) determining a sequential order for the candidate propensity score models, and (ii) evaluating at least some of the candidate propensity score models based on the sequential order.

In some implementations, the sequential order can be determined based on a complexity of each of the candidate propensity score models.

In some implementations, the sequential order can be determined based on a statistical complexity of each of the candidate propensity score models.

Selecting the set of propensity score models also includes selecting the set of propensity score models based on the sequential evaluation of at least some of the candidate propensity score models (404b).

In some implementations, the set of propensity score models can include a single propensity score model only.

In some implementations, the set of propensity score models can include a plurality of propensity score models.

In some implementations, the output of the candidate propensity score model can represent a standardized difference of each of one or more covariates of the candidate propensity score model.

In some implementations, the one or more stop criteria can include a determination that the standardized difference of each of the one or more covariates of the candidate propensity score model is less than a threshold value.

In some implementations, the one or more stop criteria can include a determination that a number of evaluated candidate propensity score models is greater than or equal to a threshold value.

The system stores a data structure representing the set of propensity score models using the one or more hardware storage devices (406).

The system outputs the data structure (408). For example, the system can cause a user interface to be presented to a user, where the user interface includes an indication of the set of propensity score models.

Further, the effectiveness of the treatment can be estimated based on the set of propensity score models (410). In some implementations, estimating the effectiveness of the treatment of the clinical study can include minimizing, based on the at least one propensity score model of the set of propensity score models, a selection bias associated with an estimation of an effect of the treatment.

In some implementations, the process 400 can also include conducting a clinical study based on the data structure (e.g., based on the selected propensity score model(s) and/or the propensity scores generated by those model(s)).

In some implementations, the process 400 can also include modifying the treatment of one or more additional subjects based on the data structure (e.g., based on the selected propensity score model(s) and/or the propensity scores generated by those model(s)).

In some implementations, the process 400 can also include receiving user input representing one or more selection criteria, and selecting at least some of the candidate propensity score models based on the one or more selection criteria.

Example Computer Systems

Figure 5:
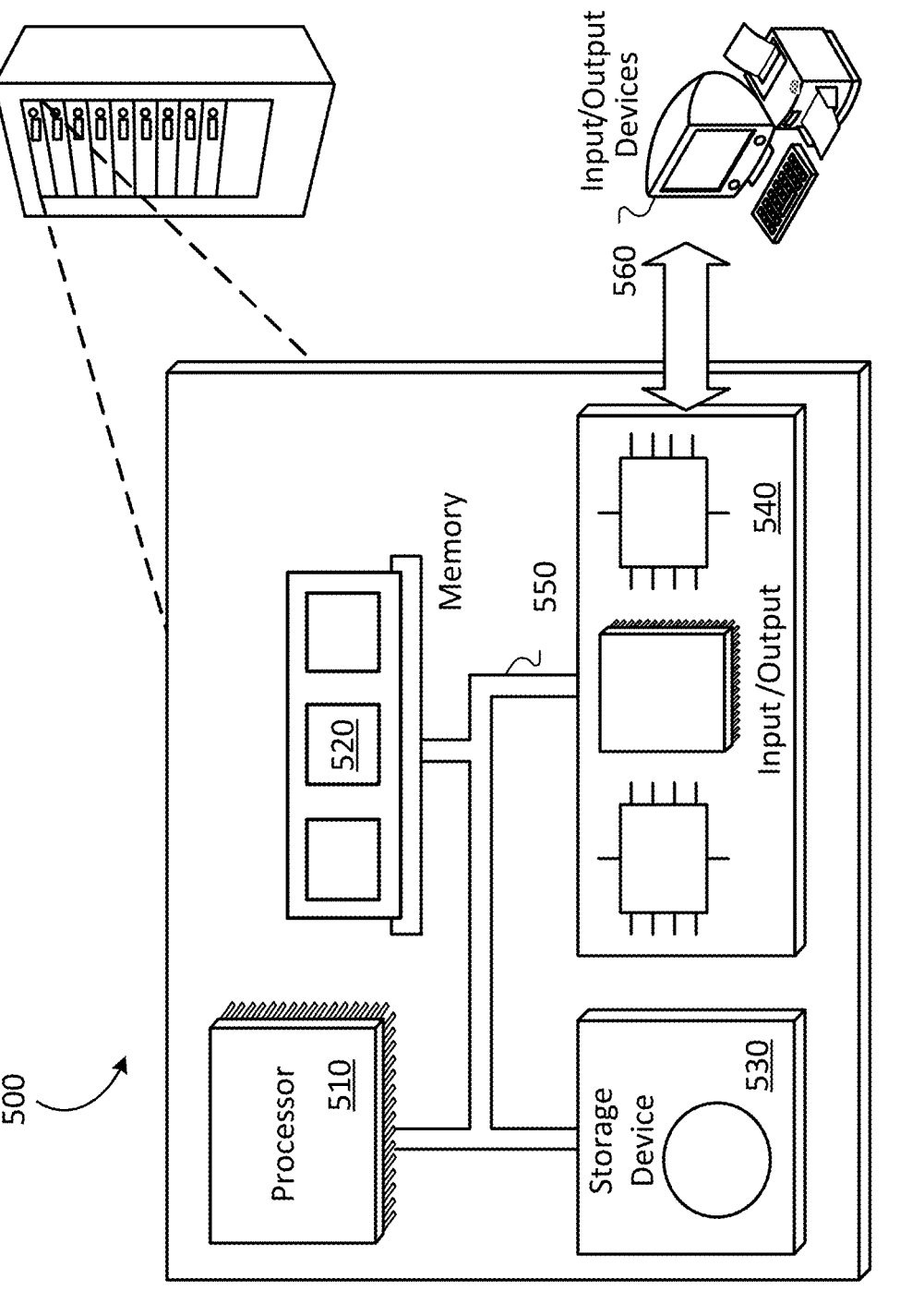
FIG. 5 is a diagram of an example computer system.

FIG. 5 depicts an example computing system, according to implementations of the present disclosure. The system 500 may be used for any of the operations described with respect to the various implementations discussed herein. The system 500 may include one or more processors 510, a memory 520, one or more storage devices 530, and one or more input/output (I/O) devices 560 controllable through one or more I/O interfaces 540. The various components 510, 520, 530, 540, or 560 may be interconnected through at least one system bus 550, which may enable the transfer of data between the various modules and components of the system 500.

The processor(s) 510 may be configured to process instructions for execution within the system 500. The processor(s) 510 may include single-threaded processor(s), multi-threaded processor(s), or both. The processor(s) 510 may be configured to process instructions stored in the memory 520 or on the storage device(s) 530. The processor(s) 510 may include hardware-based processor(s) each including one or more cores. The processor(s) 510 may include general purpose processor(s), special purpose processor(s), or both.

The memory 520 may store information within the system 500. In some implementations, the memory 520 includes one or more computer-readable media. The memory 520 may include any number of volatile memory units, any number of non-volatile memory units, or both volatile and non-volatile memory units. The memory 520 may include read-only memory, random access memory, or both. In some examples, the memory 520 may be employed as active or physical memory by one or more executing software modules.

The storage device(s) 530 may be configured to provide (e.g., persistent) mass storage for the system 500. In some implementations, the storage device(s) 530 may include one or more computer-readable media. For example, the storage device(s) 530 may include a floppy disk device, a hard disk device, an optical disk device, or a tape device. The storage device(s) 530 may include read-only memory, random access memory, or both. The storage device(s) 530 may include one or more of an internal hard drive, an external hard drive, or a removable drive.

One or both of the memory 520 or the storage device(s) 530 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 500. In some implementations, the CRSM may include a data store that provides storage of computer-readable instructions or other information in a non-transitory format. The CRSM may be incorporated into the system 500 or may be external with respect to the system 500. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) 510 and the memory 520 may be supplemented by, or incorporated into, one or more application-specific integrated circuits (ASICs).

The system 500 may include one or more I/O devices 560. The I/O device(s) 560 may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) 560 may also include one or more output devices such as a display, LED(s), an audio output device (e.g., a speaker), a printer, a haptic output device, and so forth. The I/O device(s) 560 may be physically incorporated in one or more computing devices of the system 500 or may be external with respect to one or more computing devices of the system 500.

The system 500 may include one or more I/O interfaces 540 to enable components or modules of the system 500 to control, interface with, or otherwise communicate with the I/O device(s) 560. The I/O interface(s) 540 may enable information to be transferred in or out of the system 500, or between components of the system 500, through serial communication, parallel communication, or other types of communication. For example, the I/O interface(s) 540 may comply with a version of the RS-232 standard for serial ports, or with a version of the IEEE 1284 standard for parallel ports. As another example, the I/O interface(s) 540 may be configured to provide a connection over Universal Serial Bus (USB) or Ethernet. In some examples, the I/O interface(s) 540 may be configured to provide a serial connection that is compliant with a version of the IEEE 1394 standard.

The I/O interface(s) 540 may also include one or more network interfaces that enable communications between computing devices in the system 500, or between the system 500 and other network-connected computing systems. The network interface(s) may include one or more network interface controllers (NICs) or other types of transceiver devices configured to send and receive communications over one or more networks using any network protocol.

Computing devices of the system 500 may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 500 may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

This specification uses the term "configured" in connection with systems and computer program components. For a system of one or more computers to be configured to perform particular operations or actions means that the system has installed on software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively, or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose micro-processors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially be claimed as such, one or more features from a claimed combination can in some cases be excised from the combination, and the claimed combination may be directed to a sub combination or variation of a sub combination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A system comprising:

a memory for storing:

first data representing a plurality of characteristics of each of a plurality of test subjects, and second data representing a plurality of candidate propensity score models for estimating an effectiveness of a treatment performed on one or more of the test subjects, with the second data specifying an ordering of the plurality of candidate propensity score models; and a processor communicatively coupled to the at least one memory, wherein the processor is configured to:

access, from the memory, the first data and the second data;

select a set of propensity score models from among the plurality of candidate propensity score models, wherein selecting the set of propensity score models comprises:

automatically sequentially evaluating at least some of the candidate propensity score models until one or more stop criteria are satisfied, wherein the one or more stop criteria comprises a determination that a difference of each of one or more characteristics of the candidate propensity score model satisfies a threshold value, wherein evaluating each of the candidate propensity score models comprises:

in accordance with the second data, accessing, by the system, computer code to generate a candidate propensity score model that is ordered next in the ordering;

executing, by the system, the computer code to obtain an output of the candidate propensity score model based on at least a portion of the first data as input, and determining whether the output of the candidate propensity score model satisfies the one or more stop criteria; and selecting the set of propensity score models based on the sequential evaluation of at least some of the candidate propensity score models;

store, using the memory, a data structure representing the set of propensity score models; and output the data structure, wherein outputting the data structure comprises causing a user interface to be presented to a user, wherein the user interface comprises an indication of the set of propensity score models.

2. The system of claim 1, wherein the system is further configured to:

estimate the effectiveness of the treatment based on the set of propensity score models.

3. A method comprising:

accessing, by a computer system from one or more hardware storage devices:

first data representing a plurality of characteristics of each of a plurality of test subjects, and second data representing a plurality of candidate propensity score models for estimating an effectiveness of a treatment of one or more of the plurality of test subjects, with the second data specifying an ordering of the plurality of candidate propensity score models;

selecting, by the computer system, a set of propensity score models from among the plurality of candidate propensity score models, wherein selecting the set of propensity score models comprises:

automatically sequentially evaluating by the computer system at least some of the candidate propensity score models until one or more stop criteria are satisfied, wherein the one or more stop criteria comprises a determination that a difference of each of one or more characteristics of the candidate propensity score model satisfies a threshold value, wherein evaluating each of the candidate propensity score models comprises:

in accordance with the second data, accessing, by the computer system, computer code to generate a candidate propensity score model that is ordered next in the ordering;

executing, by the computer system, the computer code to obtain an output of the candidate propensity score model based on at least a portion of the first data as input, and determining whether the output of the candidate propensity score model satisfies the one or more stop criteria; and selecting the set of propensity score models based on the sequential evaluation of at least some of the candidate propensity score models;

storing, by the computer system, a data structure representing the set of propensity score models using the one or more hardware storage devices; and outputting, by the computer system, the data structure, wherein outputting the data structure comprises causing, by the computer system, a user interface to be presented to a user, wherein the user interface comprises an indication of the set of propensity score models.

4. The method of claim 3, further comprising estimating the effectiveness of the treatment based on the set of propensity score models.

5. The method of claim 4, wherein estimating the effectiveness of the treatment of the clinical study comprises:

minimizing, based on the at least one propensity score model of the set of propensity score models, a selection bias associated with an estimation of an effect of the treatment.

6. The method of claim 3, further comprising:

conducting a clinical study based on the data structure.

7. The method of claim 3, further comprising:

modifying the treatment of one or more additional subjects based on the data structure.

8. The method of claim 3, wherein the set of propensity score models consists of one propensity score model.

9. The method of claim 3, wherein the set of propensity score models comprises a plurality of propensity score models.

10. The method of claim 3, wherein sequentially evaluating at least some of the candidate propensity score models comprises:

determining a sequential order for the candidate propensity score models, and evaluating at least some of the candidate propensity score models based on the sequential order.

11. The method of claim 9, wherein the sequential order is determined based on a complexity of each of the candidate propensity score models.

12. The method of claim 9, wherein the sequential order is determined based on a statistical complexity of each of the candidate propensity score models.

13. The method of claim 2, wherein the output of the candidate propensity score model represents a standardized difference of each of one or more covariates of the candidate propensity score model.

14. The method of claim 12, wherein the one or more stop criteria comprises a determination that the standardized difference of each of the one or more covariates of the candidate propensity score model is less than a threshold value.

15. The method of claim 12, wherein the one or more stop criteria comprises a determination that a number of evaluated candidate propensity score models is greater than or equal to a threshold value.

16. The method of claim 14, wherein the data structure comprises a tabular structured data file including a grid of data cells, wherein the data cells are arranged according to a plurality of rows and a plurality of columns, and wherein the data cells represent:

at least one of the candidate propensity score models, and at least one of the standardized differences corresponding to at least one of the candidate propensity score models.

17. The method of claim 3, further comprising:

receiving user input representing one or more selection criteria, and selecting at least some of the candidate propensity score models based on the one or more selection criteria.

18. The method of claim 3, wherein each of the candidate propensity score models is configured to generate a respective propensity score based on at least a portion of the first data, and wherein the propensity score represents a probability that a particular test subject has been administered the treatment based on the characteristics of that test subject.

19. One or more non-transitory computer-readable media storing instructions which, when executed by at least one processor, cause the at least one processor to perform operations comprising:

accessing, from one or more hardware storage devices:

first data representing a plurality of characteristics of each of a plurality of test subjects, and second data representing a plurality of candidate propensity score models for estimating an effectiveness of a treatment of one or more of the plurality of test subjects, with the second data specifying an ordering of the plurality of candidate propensity score models;

selecting a set of propensity score models from among the plurality of candidate propensity score models, wherein selecting the set of propensity score models comprises:

automatically sequentially evaluating at least some of the candidate propensity score models until one or more stop criteria are satisfied, wherein the one or more stop criteria comprises a determination that a difference of each of one or more characteristics of the candidate propensity score model satisfies a threshold value, wherein evaluating each of the candidate propensity score models comprises:

in accordance with the second data, accessing computer code to generate a candidate propensity score model that is ordered next in the ordering;

executing the computer code to obtain an output of the candidate propensity score model based on at least a portion of the first data as input, and determining whether the output of the candidate propensity score model satisfies the one or more stop criteria; and selecting the set of propensity score models based on the sequential evaluation of at least some of the candidate propensity score models;

storing a data structure representing the set of propensity score models using the one or more hardware storage devices; and outputting the data structure, wherein outputting the data structure comprises causing a user interface to be presented to a user, wherein the user interface comprises an indication of the set of propensity score models.

20. The one or more non-transitory computer-readable media of claim 19, wherein the operations further comprise:

estimating the effectiveness of the treatment based on the set of propensity score models.

* * * * *